United States Patent [19]

Nardi et al.

[11] 4,438,133
[45] Mar. 20, 1984

[54] THERAPEUTICALLY EFFECTIVE DERIVATIVES OF CYSTINE

[75] Inventors: Dante Nardi; Alberto Tajana; Gianni Motta; Pietro Cazzulani; Gabriele Graziani, all of Milan, Italy

[73] Assignee: Recordati S.A., Chiasso, Switzerland

[21] Appl. No.: 392,806

[22] Filed: Jun. 28, 1982

[30] Foreign Application Priority Data

Jul. 7, 1981 [GB] United Kingdom ............... 8120907

[51] Int. Cl.$^3$ ............... C07C 143/78; C07C 125/073; A61K 31/18; A61K 31/27
[52] U.S. Cl. ................................ 424/300; 560/16; 564/82; 424/321
[58] Field of Search ............... 560/16; 564/82; 424/300, 321

[56] References Cited

U.S. PATENT DOCUMENTS 2,723,972 11/1955 Herrick ................... 560/16
4,185,114 1/1980 Barrelle ................... 560/16

OTHER PUBLICATIONS

Taniyama, Chem. Abst., 54:18480, (1960).

Roberts, "Basic Principles of Organic Chemistry", pp. 664–665, (1963).

*Primary Examiner*—Michael L. Shippen
*Attorney, Agent, or Firm*—Burns, Doane, Swecker & Mathis

[57] ABSTRACT

Novel cystine derivatives having the structural formula (I):

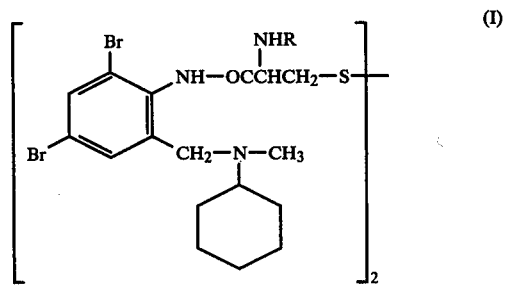

wherein R is benzyloxycarbonyl or tosyl, and the pharmaceutically acceptable acid addition salts thereof, are effective expectorants and antitussives, and are also effective for the liquescence of respiratory tract fluids.

10 Claims, No Drawings

THERAPEUTICALLY EFFECTIVE DERIVATIVES OF CYSTINE

BACKGROUND OF THE INVENTION

Field of the Invention

The present invention relates to certain novel amino/amide derivatives of cystine, to the pharmaceutically acceptable salts and process for the preparation thereof, and to various therapeutically effective pharmaceutical compositions comprising same.

SUMMARY OF THE INVENTION

The present invention features certain novel amino/amide derivatives of cystine having the following structural formula (I):

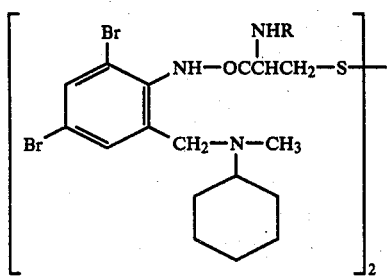

wherein R is benzyloxycarbonyl or tosyl, and pharmaceutically acceptable acid addition salts thereof.

This invention also features a process for the preparation of the subject cystine derivatives having the structural formula (I), by reacting a cystyl dichloride having the structural formula (II):

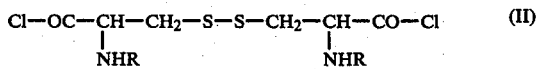

with 2,4-dibromo-6-(N-methyl-N-cyclohexyl-aminomethyl)-aniline (hereinafter "bromhexine").

DETAILED DESCRIPTION OF THE INVENTION

More particularly according to this invention, the cystyl dichloride starting materials having the structural formula (II) are themselves conveniently obtained from the corresponding acids thereof via any of the conventional and typical methods for conversion of an acid into the acid chloride form thereof, for example, by treatment with phosphorus pentachloride in a suitable solvent, such as chloroform or diethyl ether. It is not necessary to isolate or purify the dichloride before proceeding with the method according to the invention. One suitable procedure is to precipitate the dichloride from the reaction mixture, for example, by addition of ligroin (to diethyl ether solutions) or diethyl ether (to chloroform solutions), filter it off, and add thereto a solution of bromhexine in a suitable solvent, such as chloroform or ethyl acetate. The reaction with bromhexine proceeds at ambient temperature and may, if desired, be completed under reflux. The resultant cystine derivatives according to the invention may be isolated and purified, and optionally converted into a pharmaceutically acceptable acid addition salt, by any of the conventional and usual methods, such as direct treatment with the selected acid in suitable solvent. Salts of hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, benzenesulfonic and naphthalene-2-sulfonic acids are the preferred.

The noven cystine derivatives according to this invention and the aforesaid salts thereof display good expectorant and antitussive activity, as well as being well suited for the liquescence of respiratory tract fluids. The subject compounds also display markedly low toxicity; the $LD_{50}$ value, determined in the mouse and in the rat, both i.p., and per os, is greater than 3000 mg/kg for the subject compounds.

The expectorant activity ($ED_{50}$) fo the topic cystine derivatives, determined in the rabbit according to the method of Boyd [Boyd and Sheppard, Arch. Int. Pharm., 163, 284 (1966)] was 100 mg/kg (I, R=benzyloxy-carbonyl).

The same $ED_{50}$, determined in the mouse according to an improved Mavatari method [Graziani, Cazzulani, Il Farmaco, Ed. Prat., XXXVI, 3, 167 (1981)], was respectively 1.2 mg/kg (I, R=benzyloxycarbonyl) and 3.7 mg/kg (I, R=tosyl).

The compound I (R=benzyloxycarbonyl) was demonstrated to be active i.p., as an antitussive, at a dose of 30 mg/kg [method of Charlier, Prost et al., Arch. Int. Pharm., 134, 306 (1961)] through inhalation of citric acid aerosol thereof in the guinea-pig. Such activity was determined by testing the depression of cough.

In order to evaluate the antitussive activity, another procedure was performed. The vagus nerve was stimulated and depression of cough was reported following the injection of subject compound [Pickering and Jones, Arzn. Forsch., 29, 287 (1979)]. The $ED_{50}$ of the compounds I (R=benzyloxycarbonyl and tosyl) was respectively 88 and 74 mg/kg.

Accordingly, the present invention also features a pharmaceutical composition comprising a cystine derivative having the structural formula (I), or pharmaceutically acceptable sale thereof, in admixture with conventional pharmaceutically acceptable diluent or carrier. Suitable such carriers will be apparent to those skilled in this art. Compare, for example, Remington's Pharmaceutical Sciences, 4th Edition (1970).

In order to further illustrate the present invention and the advantages thereof, the following specific examples are given, it being understood that same are intended only as illustrative and in nowise limitative.

EXAMPLE 1

N,N'-ditosyl;-cystyl-bis[2,4-dibromo-6-(N-methyl-N-cyclohexylaminoethyl)-anilide]

To 17.20 g of N,N'-ditosyl-L-cystine dissolved in 185 ml of diethyl ether, 18.5 g of phosphorous pentachloride were slowly added at a temperature of 20°-25° C. The mixture was stirred for 30 minutes and then 650 ml of ligroin were added. The precipitate thus formed was filtered off, and, at 20°-25° C., a solution of 27.52 g of bromhexine in 74 ml of chloroform was added thereto. The mixture was permitted to stand at the above temperature for 36 hours. The entire reaction mass was extracted with chloroform and washed, first with sodium carbonate, and then with water. The organic layer was dried with calcium chloride. The solvent was evaporated off and the residue was purified on a silica column, using chloroform: ethyl acetate (3:2 by volume) as eluent. The unreacted bromhexine was separated off. The product, as free base, was dried, dissolved in isopropanol and directly transformed into its hydrochloride by adding hydrogen chloride in isopropanol and then diethyl ether.

The precipitate was crystallized from 95% ethanol and diethyl ether; Mp 191°-192° C.

| Elemental analysis for $C_{48}H_{60}Br_4N_6O_6S_4.2HCl.2H_2O$ | | | | | | |
|---|---|---|---|---|---|---|
| | C | H | N | Cl | S | Br | H₂O |
| Calculated (%) | 41.96 | 4.66 | 6.11 | 5.16 | 9.33 | 23.26 | 2.76 |
| Found (%) | 41.91 | 4.83 | 5.96 | 5.30 | 9.54 | 23.25 | 2.62 |

EXAMPLE 2

N,N'dibenzyloxycarbonyl-cystyl-bis[2,4-dibromo-6-(N-methyl-N-cyclohexyl-aminomethyl)-anilide]:

To 10.16 g of N,N'-dibenzyloxycarbonyl-L-cystine dissolved in 56 ml of anhydrous chloroform, 10 g of phosphorus pentachloride were slowly added at a temperature of from −10° C. to −5° C.

The reaction mixture was stirred for 10 minutes and then 60 ml of diethyl ether were added thereto. The entire reaction mass was cooled for one hour. The precipitate thus formed was filtered off and, at 22° C., a solution of 14.88 g of bromhexine in 40 ml of ethyl acetate was added thereto. The mixture was stirred at the above temperature for one day and then refluxed for 4 hours.

Upon completion of the reaction, the mixture was extracted with ethyl acetate, washed with sodium carbonate solution, next with water, and then dried over anhydrous sodium sulfate. The solvent was evaporated off and the residue was treated with hexane. The product was filtered, collected, and crystallized from ethanol; Mp 168° C.

Adding hydrogen chloride in ethanol thereto, the corresponding salt, melting at 195°-197° C. (with decomposition) was obtained.

| Elemental analysis for $C_{50}H_{60}Br_4N_6O_6S_2.2HCl$ | | | | | | |
|---|---|---|---|---|---|---|
| | C | H | N | Br | Cl | S |
| Calculated (%) | 46.28 | 4.81 | 6.47 | 24.63 | 5.46 | 4.94 |
| Found (%) | 45.94 | 4.79 | 6.27 | 24.97 | 5.13 | 4.82 |

Utilizing the same procedures as above, but changing the acid used for salt formation, the following salts were prepared:
(i) Hydrobromide: mp 190°-195° C.
(ii) Formate: mp 167°-169° C.
(iii) Mandelate: mp 148°-149° C.
(iv) Acetate: mp 169°-171° C.
(v) Tartrate: mp 131°-134° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. An amino/amide derivative of cystine having the structural formula (I):

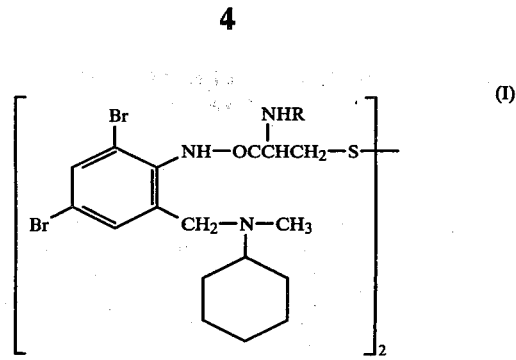

wherein R is benzyloxycarbonyl or tosyl, or a pharmaceutically acceptable acid addition salt thereof.

2. A cystine derivative as defined by claim 1, the same being N,N'-ditosyl-cystyl-bis[2,4-dibromo-6-(N-methyl-N-cyclohexyl-aminomethyl)-anilide], or pharmaceutically acceptable acid addition salt thereof.

3. A cystine derivative as defined by claim 1, the same being N,N'-dibenzyloxycarbony-cystyl-bis[2,4-dibromo-6-(N-methyl-N-cyclohexyl-aminomethyl)-anilide], or pharmaceutically acceptable acid addition salt thereof.

4. A composition of matter comprising an antitussively, expectoranty or respiratory tract fluid liquescence effective amount of the cystine derivative as defined by claim 1, or pharmaceutically acceptable acid addition salt thereof, and a pharmaceutically acceptable carrier therefor.

5. A method for eliciting an antitussive response in a warm-blooded mammal, comprising administering to a warm-blooded mammal in need of such treatment, an antitussively effective amount of an amino/amide derivative of cystine having the structural formula (I):

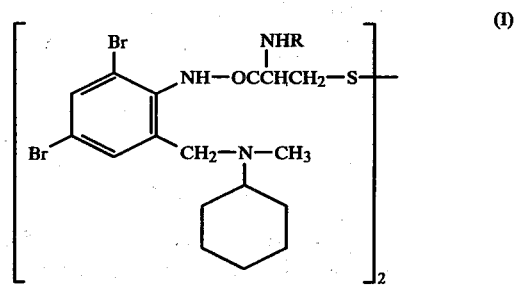

wherein R is benzyloxycarbonyl or tosyl, or a pharmaceutically acceptable acid addition salt thereof.

6. The method of eliciting an antitussive response in a warm-blooded mammal in accordance with claim 5, wherein the cystine derivative or pharmaceutically acceptable acid addition salt thereof is in admixture with a pharmaceutically acceptable carrier therefor.

7. A method for eliciting an expectorant response in a warm-blooded mammal, comprising administering to a warm-blooded mammal in need of such treatment, an expectorantly effective amount of an amino/amide derivative of cystine having the structural formula (I):

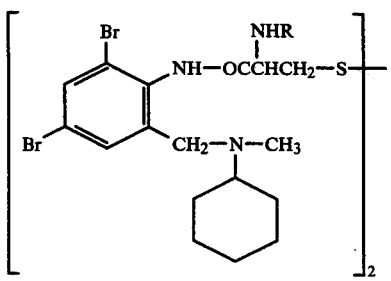

(I)

wherein R is benzyloxycarbonyl or tosyl, or a pharmaceutically acceptable acid addition salt thereof.

8. The method for eliciting an expectorant response in a warm-blooded mammal in accordance with claim 7, wherein the cystine derivative or pharmaceutically acceptable acid addition salt thereof is in admixture with a pharmaceutically acceptable carrier therefor.

9. A method for eliciting a respiratory tract fluid liquescence response in a warm-blooded mammal, comprising administering to a warm-blooded mammal in need of such treatment, a respiratory tract fluid liquescence effective amount of an amino/amide derivative of cystine having the structural formula (I):

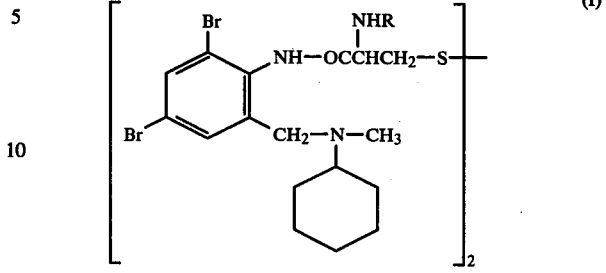

(I)

wherein R is benzyloxycarbonyl or tosyl, or a pharmaceutically acceptable acid addition salt thereof.

10. The method for eliciting a respiratory tract fluid liquescence response in a warm-blooded mammal in accordance with claim 9, wherein the cystine derivative or pharmaceutically acceptable acid addition salt thereof is in admixture with a pharmaceutically acceptable carrier therefor.

* * * * *